United States Patent [19]
Deagle et al.

[11] Patent Number: 4,765,310
[45] Date of Patent: Aug. 23, 1988

[54] ELECTRICAL AND MAGNETIC PAIN TREATMENT DEVICE

[75] Inventors: William R. Deagle, Calgary; Gary E. Gunthrpe, Bassano, both of Canada

[73] Assignee: Dynatens Research Corporation, Calgary, Canada

[21] Appl. No.: 924,314

[22] Filed: Oct. 29, 1986

[30] Foreign Application Priority Data

Nov. 1, 1985 [CA] Canada ................... 494447

[51] Int. Cl.$^4$ ............................................. A61B 17/52
[52] U.S. Cl. ..................................... 128/1.5; 128/421
[58] Field of Search ................ 128/1.5, 419 R, 420 R, 128/421

[56] References Cited

U.S. PATENT DOCUMENTS

| | | |
|---|---|---|
| 2,656,839 | 10/1953 | Howard . |
| 3,848,588 | 11/1974 | Miquel ................... 128/1.5 |
| 3,900,020 | 8/1975 | Lock . |
| 3,915,151 | 10/1975 | Kraus ................... 128/1.5 |
| 4,112,923 | 9/1978 | Tomecek ................... 128/419 R |
| 4,155,366 | 5/1979 | Di Mucci ................... 128/421 |
| 4,197,851 | 4/1980 | Fellus . |
| 4,233,965 | 11/1980 | Fairbanks ................... 128/420 R |
| 4,289,136 | 9/1981 | Rienzo, Sr. . |
| 4,454,883 | 6/1984 | Fellus ................... 128/1.5 |

FOREIGN PATENT DOCUMENTS

| | | | |
|---|---|---|---|
| 0143748 | 6/1985 | European Pat. Off. | ............ 128/421 |
| 1416141 | 12/1975 | United Kingdom | ............ 128/419 R |

*Primary Examiner*—Max Hindenburg
*Attorney, Agent, or Firm*—Hoffman, Wasson & Fallow

[57] ABSTRACT

Apparatus for alleviation of pain in a patient comprises a treatment head and a cabinet which houses driving and control circuitry for the treatment head. The treatment head has a central electrode and an outer electrode arranged concentrically with respect to the central electrode. The central electrode has a portion which extends inwardly and serves as a ferromagnetic core around which are wound two insulated coils. The driving and control circuitry produces pulses of electricity in one of the coils which produces magnetic field pulses having a force field which extends externally of the treatment head in the vicinity of the electrodes. These magnetic pulses induce in the other coil electric voltage pulses at the rise and fall of the magnetic pulses and these electric voltage pulses are conveyed to the electrodes. The combined magnetic and electric voltage pulses provides greater relief which lasts longer than either magnetic or electric fields applied alone.

5 Claims, 2 Drawing Sheets

ELECTRICAL AND MAGNETIC PAIN TREATMENT DEVICE

BACKGROUND OF THE INVENTION

This invention relates to apparatus for alleviating pain in a patient.

A pain treatment procedure commonly known as Transcutaneous-Electrical-Nerve-Stimulation (TENS) has been used on and off for about 20 years with limited short term pain relief. Physiotherapists are the largest users as the devices tend to provide short term pain relief (1–4 hours) allowing the therapist to provide other physical therapy.

TENS therapy has been thought to over stimulate the nerve receptors, thus fatiguing them and blocking transmission of pain impulses.

In Europe (primarily Germany and U.S.S.R.), a slowly pulsing strong magnetic field had been used to treat pain and swelling of arthritis. Recent work in North America has shown that a similar magnetic field promoted healing of bone breaks. Also a small trickle of electrical current across the break was found to produce enhanced healing.

SUMMARY OF THE INVENTION

It was felt by the inventors that these bone healing techniques produced a concentration of ions at the injury, also that TENS actually worked in a similar manner by creating the sodium and magnesium ions used by the body to regulate nerve impulses and that by combining the ionic concentration effects of the magnetic field with TENS would enhance the pain relief.

According to a broad aspect of the present invention, therefore, there is provided apparatus for the alleviation of pain in a patient, comprising a treatment head for application to the patient and having at least one pair of spaced electrodes, means for generating in the treatment head magnetic field pulses having a force field which extends externally of the treatment head in the vicinity of the electrodes, and means for generating substantially simultaneously with the magnetic field pulses electrical voltage pulses across the pair of electrodes.

In a preferred embodiment of the invention the pair of spaced electrodes comprises a central electrode and an outer electrode arranged concentrically with respect to the central electrode. Predetermining the spacing of the two electrodes in this way prevents current from passing through the heart which could occur with two completely separate electrodes. In this embodiment, the central electrode has a portion which extends inwardly of the treatment head and serves as a ferromagnetic core around which a coil producing the magnetic pulses is wound.

Preferably, the electrical voltage pulses are induced in a second coil wound around the first coil and insulated therefrom. This way of obtaining the electric voltage pulses provides a high degree of electrical insulation.

Rudimentary studies performed to date indicate that the combined and simultaneous treatment provides a substantially greater degree of pain relief which lasts longer (sometimes permanently) than either TENS or magnetic field therapy alone. Also the level of electrical voltage used can be substantially reduced (as compared to that used in TENS). This reduces the electrical shock (pain) induced during treatment and eliminates the possibility of nerve or tissue damage.

BRIEF DESCRIPTION OF THE DRAWINGS

The invention will now be described with reference to the accompanying drawings, in which.

DESCRIPTION OF THE PREFERRED EMBODIMENT

Figure 1:
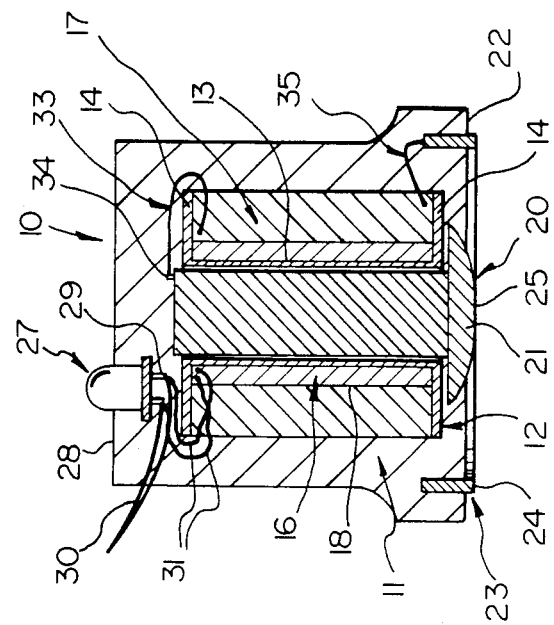
FIG. 1 is a somewhat schematic sectional view of a treatment head according to the invention.

With reference firstly to FIG. 1, the treatment head 10 comprises a generally cylindrical body 11 made of polyurethane or other insulating material in which is embedded a coil form 12 formed of polyurethane or nylon and having a central tubular portion 13 and two end flanges 14. An inner coil 16 formed, for example, of 250 turns of 32 gauge coated copper wire is wound hard against the tubular portion 13 and an outer coil 17 formed, for example, of 1750 turns of 32 gauge coated copper wire is wound around the inner coil 16 but separated therefrom by a layer of insulation tape 18.

A chromium plated steel carriage bolt 20, for example 5/16"×1", is received snugly in the bore of the tubular portion 13 with the head 21 of the bolt projecting partly from the bottom surface 22 of the cylindrical body 11. A ring 23 made, for example, from a 3/16" long portion of 1" diameter chromium plated copper tubing, is also embedded in the polyurethane body and projects from the bottom surface 22 of body 11. The ring 23 is positioned concentrically with respect to the head 21 of the bolt 20 and the lower edge 24 of the ring is substantially coplanar with the lowermost surface portion 25 of head 21. The head 21 serves as a central electrode and the ring 23 as an outer electrode arranged concentrically with respect to the central electrode.

An L.E.D. 27 is also embedded in body 11 but it projects from the top surface 28 of the body. The LED has a pair of terminals 29 connected to a coaxial cable 30 which is connected to an output jack of a cabinet (not shown) which houses the driving and control circuitry for the treatment head. The terminals 29 are connected by a pair of leads 31 to opposite electrical ends of the inner coil. One electrical end of the outer coil 17 is connected by means of a lead 33 to a terminal 34 on the uppermost end of bolt 20 and the other electrical end of the outer coil 17 is connected by means of a lead 35 to the ring 23.

Figure 2:
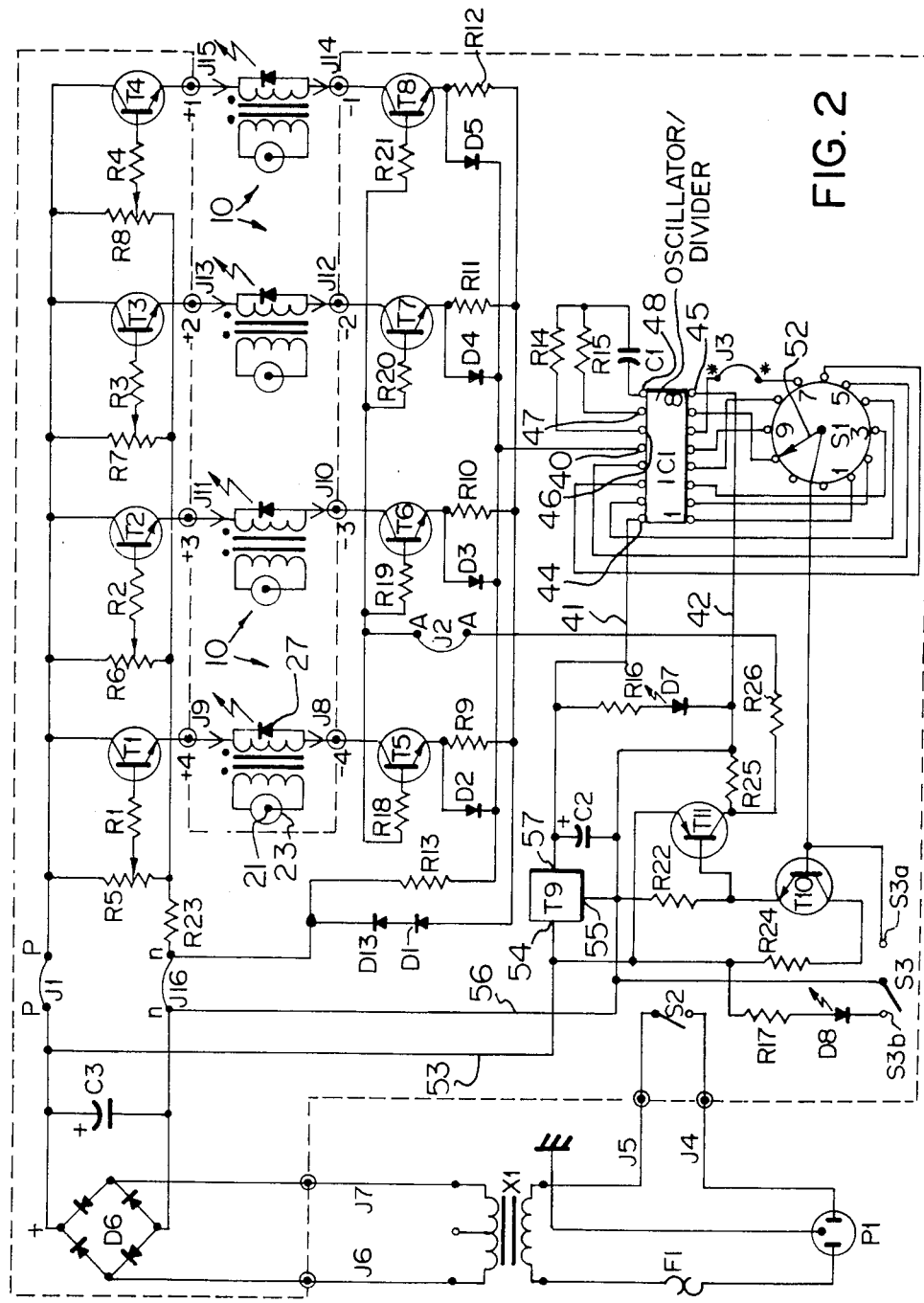
FIG. 2 is a schematic diagram of the circuitry for driving four separate treatment heads.

Referring now to FIG. 2, this shows within the broken outline the driving and control circuitry within the cabinet referred to above. Also shown schematically are four treatment heads and an input power transformer.

The input power transformer X1 has a primary circuit containing a power outlet plug P1, fuse F1 and switch S2, which is mounted in the cabinet and connected to the primary circuit via jacks J4 and J5. The secondary side of the transformer X1 is connected through jacks J6 and J7 to a rectifying and smoothing circuit comprising a diode bridge D6 and a capacitor C3. The primary voltage is 110 volts A.C. and the rectified voltage is 24 volts D.C. To the output side of the rectifying and smoothing circuit are connected in parallel variable resistors R5-R8. The tap of each resistor R5-R8 is connected through a respective resistor R1-R4 to the base of a respective transistor T1-T4 the collectors of which are all connected in common to the positive side of resistors R5-R8 and the emitters of which are connected respectively to output jacks J9, J11, J13 and J15.

The negative side of the rectifying and smoothing circuit is connected through a resistor R13 and respective diodes D2-D5 to the emitters of transistors T5-T8. The negative side of the rectifying and smoothing circuit is also connected through diodes D13 and D1 and respective resistors R9-R12 to the emitters of transistors T5-T8. The bases of these transistors are connected in common through respective resistors R18-R21 to one side of a resistor R26 via jumper J2. The collectors of transistors T5-T8 are connected respectively to output jacks J8, J10, J12 and J14.

The junction of diodes D2-D5 with resistor R13 is connected to a reset input 40 of an integrated circuit oscillator/divider IC1 which is powered by leads 41 and 42 which are connected respectively to power inputs 44 and 45 of IC1. Resistors R14, R15 and capacitor C1 are connected together at one end and have their other ends respectively connected to inputs 46, 47 and 48 of IC1. The remaining nine terminals of IC1 are all outputs which are respectively connected to the nine inputs of a rotary switch S1 which has a movable contact 52 connected to the base of a transistor T10 and a stationary contact S3a of a switch S3.

The positive side of the rectifying and smoothing circuit is connected via lead 53 to an input 54 of a voltage regulator T9 and the negative side is connected to another input 55 via a lead 56 of regulator T9. Power leads 41 and 42 which, as indicated above are connected to power input terminals 44 and 45 of IC1, are connected, respectively, to an output terminal 57 of regulator T9 and to input 55. Voltage regulator T9 provides a smooth 5 volts D.C. from the rectified 24 volts obtained by the rectifying circuit. A capacitor C2 is connected between lines 41 and 42 as is the series combination of a resistor R16 and an LED D7.

As indicated above, the base of transistor T10 is connected to the stationary contact S3a of switch S3. The emitter of transistor T10 is connected through a resistor R22 to lead 56 and the collector of transistor T10 is connected through a resistor R24 to lead 53. A further transistor T11 is provided, having a base connected to the emitter of transistor T10, emitter connected to lead 53 and collector connected through a resistor R25 to lead 56. It will be remembered from the above description that one side of resistor R26 is connected to transistors T5-T8. The other side of resistor R26 is connected to the collector of transistor T11. In the embodiment illustrated, transistor T11 is a PNP transistor, all the other being NPN transistors.

Finally, the positive side of the rectifying circuit is connected via lead 53, a resistor R17 and an LED D8 to a stationary contact S3b of switch S3, the movable contact of which is connected to the negative side through lead 56.

As can be seen in FIG. 2 up to four treatment heads 10 can be driven simultaneously by the circuitry. It should be understood that each pair of jacks J8 and J9, J10 and J11, J12 and J13, and J14 and J15 is actually formed as a coaxial jack for receiving a coaxial plug (not shown) terminating the coaxial cable 30 shown in FIG. 1. The heads are all identical and the inner and outer coils 16 and 17 bolt head 25, copper ring 23 and LED 27 are all shown diagrammatically.

Closure of S2 causes transformer X1 to be energized and 5 volts D.C. to be applied to terminals 44 and 45 of IC1. LED D7 ignites indicating "power on". Switch S3 is then closed causing energization of transistors T10 and T11 and also energizing LED D8 indicating "treatment on".

Transistors T10 and T11 provide gain and voltage matching between the selected (by switch S1) output of IC1 and transistors T5-T8. The oscillator output after passing through transistors T10 and T11 appears at the bases of transistors T5-T8 via jumper J2.

Meanwhile, inner or primary coils 16 of the heads 10 are being energized through transistors T1-T4 and transistors T5-T8 and the current (which equates directly to field strength) is monitored by monitoring the voltage on resistors R9-R12. When a preset magnitude is reached the oscillator/divider IC1 is reset by a signal passing through diodes D2-D5 to the reset input 40. This produces a sharply increasing and decreasing magnetic field. The back EMF produced by the collapsing magnetic field shorts through the LED's 27, thereby producing an indication that the magnetic fields have been produced.

Figure 3:
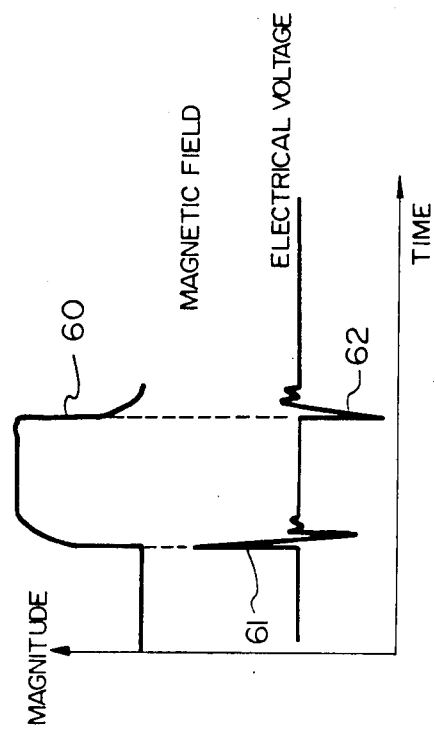
FIG. 3 is a timing diagram showing the occurrence of magnetic pulses and the consequent occurrence of electrical voltage pulses derived by the treatment heads.

The sharply increasing and decreasing magnetic field is illustrated in FIG. 3 as a magnetic pulse 60 which is applied to the patient's skin in the sense that the North polarity is towards the skin. As can be seen in FIG. 3, as the magnetic field increases an electrical voltage pulse 61 is induced in the outer or secondary coil 17 and applied across the central and concentric electrodes, with the central electrode being positive. As the magnetic pulse collapses a second, opposite polarity electrical voltage pulse 62 is induced in coil 17 which is again applied across the central and concentric electrodes. However, this time the outer electrode becomes positive.

It is believed that by applying the magnetic North down towards the patient's skin the effect is more beneficial than if the polarity were reversed. Specifically, patients have reported that a soothing warm sensation is produced rather than a painful sensation when South is down.

Typical values for the pulses used are as follows.

MAGNETIC FIELD

Repetition rate = 4 to 2000 cycles per sec.
Pulse width = $1 \times 10^{-3}$ to $1 \times 10^{-5}$ sec.
Pulse Magnitude = 0 to 10 gauss
Polarity = North pole down to skin

ELECTRICAL VOLTAGE

Repetition rate = same as magnetic field
Pulse width (both + & −) = $1 \times 10^{-4}$ to $1 \times 10^{-7}$ sec.
Pulse magnitude (both + & −) = 0 to 150 volts
Polarity
    positive on increasing mag. field
    negative on decreasing mag. field

What we claim as our invention is:

1. Apparatus for the alleviation of pain in a patient, comprising a treatment head for application to the patient and having at least one pair of spaced electrodes, means for generating in the treatment head magnetic field pulses having a force field which extends externally of the treatment head in the vicinity of the electrodes, and means for generating substantially simultaneously with the magnetic field pulses electrical voltage pulses across the pair of electrodes, the pair of spaced electrodes comprising a central electrode an an outer electrode arranged concentrically with respect to the central electrode, the central electrode having a portion which extends inwardly of the treatment head and serves as a ferromagnetic core around which a coil producing the magnetic pulses is wound.

2. Apparatus according to claim 1, in which a further coil is wound around the first mentioned coil and is insulated therefrom, the further coil being connected at opposite ends thereof across the pair of electrodes, whereby the electrical voltage pulses are induced by the magnetic field pulses produced by the first mentioned coil.

3. Apparatus according to claim 2, in which the two coils are so mutually arranged that a first electrical voltage pulse of a first polarity is induced in the further coil at a rising edge of each magnetic field pulse and a second electrical voltage pulse of the opposite polarity is induced in the further coil at a falling edge of each magnetic field pulse.

4. Apparatus according to claim 1, in which the means for generating magnetic field pulses is arranged such that the force field has a north polarity externally of the treatment head in the vicinity of the electrodes.

5. Apparatus according to claim 1, in which the magnetic field pulses have a repetition rate in the range 4 to 2000 cycles per sec., a pulse width in the range $1 \times 10^{-3}$ to $1 \times 10^{-5}$ sec., and a magnitude in the range 0 to 10 gauss and the electrical voltage pulses have a repetition rate in the range 4 to 2000 cycles per sec., a pulse width in the range $1 \times 10^{-4}$ to $1 \times 10^{-7}$ sec., and a magnitude in the range 0 to 150 volts.

* * * * *